(12) United States Patent
Sundaresan et al.

(10) Patent No.: US 8,508,240 B2
(45) Date of Patent: Aug. 13, 2013

(54) SYSTEM AND METHOD FOR SOFT-FIELD TOMOGRAPHY DATA ACQUISITION

(75) Inventors: Krishnakumar Sundaresan, Clifton Park, NY (US); Naresh Kesavan Rao, Clifton Park, NY (US); Alexander Seth Ross, Albany, NY (US)

(73) Assignee: General Electric Company, Niskayuna, NY (US)

( * ) Notice: Subject to any disclaimer, the term of this patent is extended or adjusted under 35 U.S.C. 154(b) by 328 days.

(21) Appl. No.: 13/070,294

(22) Filed: Mar. 23, 2011

(65) Prior Publication Data

US 2012/0242350 A1   Sep. 27, 2012

(51) Int. Cl.
*G01R 27/04* (2006.01)

(52) U.S. Cl.
USPC ............................. 324/629; 324/71.1; 324/663

(58) Field of Classification Search
USPC .................. 324/627–629, 602–609, 659, 663, 324/672, 681
See application file for complete search history.

(56) References Cited

U.S. PATENT DOCUMENTS

| | | | |
|---|---|---|---|
| 4,649,932 | A | 3/1987 | Smith |
| 7,116,157 | B2 | 10/2006 | Ross et al. |
| 7,630,759 | B2 | 12/2009 | Davies |
| 2006/0085048 | A1* | 4/2006 | Cory et al. ..................... 607/48 |
| 2006/0204952 | A1 | 9/2006 | Moy et al. |

FOREIGN PATENT DOCUMENTS

| | | |
|---|---|---|
| WO | 2009068961 A2 | 6/2009 |
| WO | 2010030225 A1 | 3/2010 |
| WO | 2010112825 A2 | 10/2010 |

OTHER PUBLICATIONS

Halter et al., "A Broadband High-Frequency Electrical Impedance Tomography System for Breast Imaging", IEEE Transactions on Biomedical Engineering, vol. 55, Issue 2, pp. 650-659, Feb. 2008.
Search Report and Written Opinion from corresponding EP Application No. 12160732.9-2319 dated Jul. 9, 2012.
Ross, A.S. et al, Current source design for electrical impedance tomography, Physiol. Meas., vol. 24, pp. 509-516, 2003, Institute of Physics Publishing.
Gisser D.G., et al, "Current Sources for Impedance Imaging Systems," Proc. IEEE Conf. of EMBS, vol. 12, No. 1, pp. 112-113, Nov. 90.

\* cited by examiner

*Primary Examiner* — Vincent Q Nguyen
(74) *Attorney, Agent, or Firm* — Marie-Claire B. Maple

(57) ABSTRACT

A system and method for soft-field tomography data acquisition are provided. One system includes a plurality of transducers that correspond to a plurality of channels, and an excitation driver coupled to generate excitation signals for the plurality of transducers. The system also includes a single reference excitation source from which excitations are generated and one or more derived excitation sources. The one or more derived excitation sources derive excitations from the single reference excitation source that are applied to each of the plurality of channels. The system further includes a response detector and a reduced bit digitizer in each of the plurality of channels configured to digitize a measured response difference between the measured response at one or more of the transducers and at least one of an excitation of the single reference excitation source or an excitation derived from the single reference excitation source or a separate reference.

23 Claims, 8 Drawing Sheets

SYSTEM AND METHOD FOR SOFT-FIELD TOMOGRAPHY DATA ACQUISITION

BACKGROUND

This subject matter disclosed herein relates generally to measurement devices, and more particularly to soft-field tomography systems.

Soft-field tomography, for example, Electrical Impedance Spectroscopy (EIS), also referred to as Electrical Impedance Tomography (EIT), is used to measure the internal properties, in particular, the electrical properties of materials of internal structures of an object, such as a region of a human body. Such EIS systems estimate the conductivity and/or permittivity of the materials within a volume based on current and voltage data acquired proximal a surface of a volume. For example, in a human body, the electrical properties are different for air, muscle, fat and other tissues. Moreover, the electrical properties within the body region also vary with time. Accordingly, a time-varying map of electrical properties may be formed based on the conductivity distribution within the volume.

A typical EIS system includes a plurality of transducers that may be arranged and positioned proximal a surface of the object to be studied. An excitation, such as electrical currents are applied to the transducers and a measurement device measures responses, such as the voltages at the transducers. The applied excitations and measured responses are processed to create two-dimensional or three-dimensional representations of the impedance or conductivity distribution of the object, which represents the internal electrical properties of the object.

Conventional multi-channel EIS systems require highly accurate excitation sources operating from a few hundred Hertz (Hz) to a few hundred kHz that are accurate, for example, to the order of 16-bits on each channel of the system. These excitations are applied to a number of transducers and the responses at each transducer are measured to deduce the impedance distribution within the object. Based on dispersion properties of different types of molecules, the impedance distribution across a spectrum of frequencies can be used to identify the types of molecules in the tissue. However, the use of a highly accurate excitation source on each channel increases the overall complexity of each channel.

Thus, in these conventional EIS systems, higher power requirements and more physical space are needed for the electronics. These conventional systems also have a limited bandwidth, thus limiting the capability of the system to measure higher order dispersion. Additionally, these conventional systems are also affected by variations over time and with changes in environmental conditions (e.g., temperature).

BRIEF DESCRIPTION

In accordance with one embodiment, a soft-field tomography measurement system is provided that includes a plurality of transducers configured for positioning proximate a surface of an object, wherein the plurality of transducers correspond to a plurality of channels, and an excitation driver coupled to the plurality of channels and configured to generate excitation signals for the plurality of transducers. The soft-field tomography measurement system also includes a single reference excitation source from which excitations are generated and one or more derived excitation sources, wherein one or more of the derived excitation sources may derive excitations from the single reference excitation source and the derived excitations are applied to each of the plurality of channels. The soft-field tomography measurement system further includes a response detector configured to measure a response at each of the plurality of transducers and a reduced bit digitizer in each of the plurality of channels configured to digitize a measured response difference between the measured response at one or more of the transducers and at least one of an excitation of the single reference excitation source or an excitation derived from the single reference excitation source or a separate reference.

In accordance with another embodiment, a multi-channel application specific integrated circuit (ASIC) is provided that includes a single reference excitation source configured to generate at least one excitation for driving each of a plurality of channels of a soft-field tomography system and one or more derived excitation sources, configured to generate excitations derived from the single reference excitation source. The ASIC also includes a response detector configured to measure a response at each of a plurality of transducers in each of the plurality of channels and a reduced bit digitizer having fewer bits than the number of bits of the single reference excitation source and configured to digitize an output of the response detector.

In accordance with yet another embodiment, a method for providing excitation and data acquisition for a soft-field tomography system is provided. The method includes deriving one or more excitations from at least one reference excitation source which are applied to a plurality of channels of the soft-field tomography system and measuring at least one difference between the excitation applied at one or more transducers corresponding to the plurality of channels and a reference excitation. The method also includes digitizing the measured difference using a reduced number of data bits.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

Figure 1:
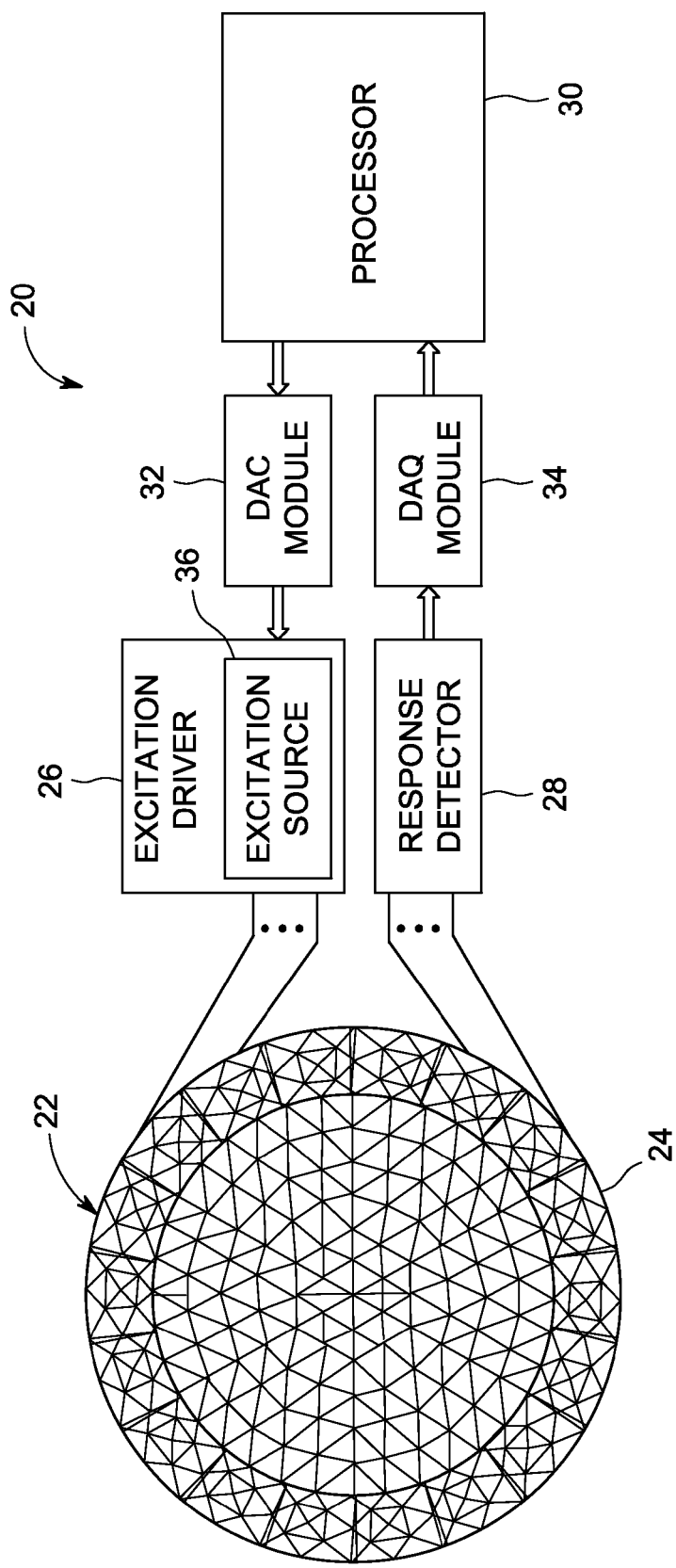
FIG. 1 is a simplified schematic block diagram illustrating a soft-field tomography system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a system and method for soft-field tomography, for example, electrical impedance spectroscopy (EIS), also referred to as electrical impedance tomography (EIT). However, the various embodiments may apply to other soft-field tomography systems, such as Diffuse Optical Tomography (DOT), Near Infrared Spectroscopy (NIRS), thermograph, electrograph or microwave tomography, and related modalities.

It should be noted that as used herein, "soft-field tomography" refers generally to any topographic or multidimensional extension of a topographic method that is not "hard-field tomography".

In general, the soft-field tomography system is illustrated as a multi-channel impedance measurement system, specifically an EIS system that includes a single reference excitation source used to generate a reference excitation (e.g., reference current) and from which are derived excitations for driving each of a plurality of transducers (e.g., electrodes) of the EIS system. For example, in one embodiment, using a single reference current source, a reference current is generated with the different currents derived from the reference current applied at each of the transducers. The individual electrode responses (e.g., voltages) to the applied currents are then measured and compared to the reference current source, which can be used to tune or calibrate the excitation applied to each of the plurality of transducers, such as to correct for the non-infinite precision in the current sources. By practicing at least one embodiment, the complexity of the measurement instrument on each channel is reduced, thereby resulting in reduced power usage and reduced physical size for the overall system.

One embodiment of an EIS system 20 is illustrated in FIG. 1. The EIS system 20 may be used to determine the electrical properties of materials within an object 22. For example, the spatial distribution of electrical conductivity ($\sigma$) and/or permittivity ($\epsilon$) may be determined inside the object 22 or other volume. Thus, internal properties of the object 22 (e.g., a patient) may be determined. In the illustrated embodiment, the system 20 includes a plurality of transducers 24 that may be positioned on the surface of the object 24 (e.g. electrodes, thermal sources, ultrasound transducers), near the surface of the object 24 (e.g., coils, radiofrequency antennas), or penetrating the surface of the object 24 (e.g., needle electrodes). Thus, the transducers 24 may take different forms, such as surface-contacting electrodes, standoff electrodes, capacitive coupled electrodes, conducting coils, and antennas, among others.

An excitation driver 26 and a response detector 28 are electrically coupled to the transducers 24 and are each connected to a processor 30 (e.g., a computing device), which may have components there between. In one embodiment, the excitation driver 26 and the response detector 28 are physically separate devices. In other embodiments, the excitation driver 26 and the response detector 28 are physically integrated as one element. The processor 20 sends instructions to the excitation driver 26 through a digital to analog converter (DAC) element 32 and receives data from the response detector 28 through a data-acquisition (DAQ) element 34.

In one embodiment, the object 22 is a human body region, such as a head, a chest, or a leg, wherein blood, air, muscle, fat and other tissues have different electrical conductivities. The electrical impedance distribution derived by the EIS system 20 shows conditions of the internal properties (e.g., material properties) of the human body region, and thus can assist in the diagnoses of diseases, for example, associated with hemorrhage, tumor, lung capacity, etc. In other embodiments, the EIS system 20 can be used for generating a visual representation of the electrical impedance distribution in a variety of other applications, such as for determining the material properties in a mixed flow including oil and water, or for investigation of an underground earth area for soil characterization.

In various embodiments, the transducers 24 are formed from any suitable conductive material used to establish a soft-field excitation (e.g., an electrical current). For example, the transducers 24 may be formed from one or more metals or alloys such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct holmic contact with the object 22 or capacitive coupled to the object 22.

In operation, the transducers 24 may be used to deliver excitations (e.g., electrical current) continuously or be modulated such that excitations may be applied across a temporal frequency range (e.g., 1 kHz to 1 MHz) to the object 22 to generate a field, for example, an electromagnetic (EM) field within the object 22. The resulting excitations, for example, surface potentials, such as the voltages on the transducers 24 are measured to determine an electrical conductivity or permittivity distribution using any suitable EIS or EIT reconstruction and/or analysis method. For example, a visual distribution may be reconstructed based on the geometry of the transducers 24, the applied currents and the measured voltages.

In various embodiments, the excitation driver 26 applies an excitation to each of the transducers 24. In one embodiment, a reference excitation source 36 and a one-to-multichannel switch (not shown) also may be provided. The single reference excitation source 36 (e.g., a current source) is used to generate an input to a plurality of derived excitation sources 62 which are transmitted in some embodiments as electrical currents to the plurality of transducers 24 as described in more detail herein. Accordingly, different derived versions of the reference excitation (e.g., scaled or frequency/phase shifted version of the reference current) are applied to each of the transducers 24. It should be noted that the excitation driver 26 may apply a direct current or an alternating current to each of the transducers 24 in some embodiments. In the illustrated embodiment for imaging a human body region, the electrical current applied to the transducers 24 is sufficient to generate an EIS distribution of the human body region. In another embodiment, the excitation driver 26 may include at least one voltage source for applying a voltage to each of the transducers 24.

In some embodiments, the response detector 28 measures a response on each of the transducers 24 (which may be multiplexed by a multiplexer) in response to the excitation applied on the transducers 24. In one embodiment, the response detector 28 includes a voltage sensor or a current sensor measuring a response voltage or a response current on the transducers 24 in response to the current or voltage applied by the excitation driver 26. The response detector 28 also may include a multi-channel analog-signal-conditioning-circuit (not shown) that amplifies and/or filters the measured response voltage or current. In other embodiments, the processor 30 includes a signal conditioning circuit for amplifying and/or filtering the response voltage or response current received from the response detector 28.

In one embodiment, the response detector 28 can communicate the measured response data to the processor 30 in real-time. Thus, in some embodiments, the response detector 28 sends the response voltage or current to the processor 30 without perceptible delay, except for the time period for processing the data. In other embodiments, the response detector 28 communicates with the processor 30 at determined time intervals to communicate the acquired data.

Figure 2:
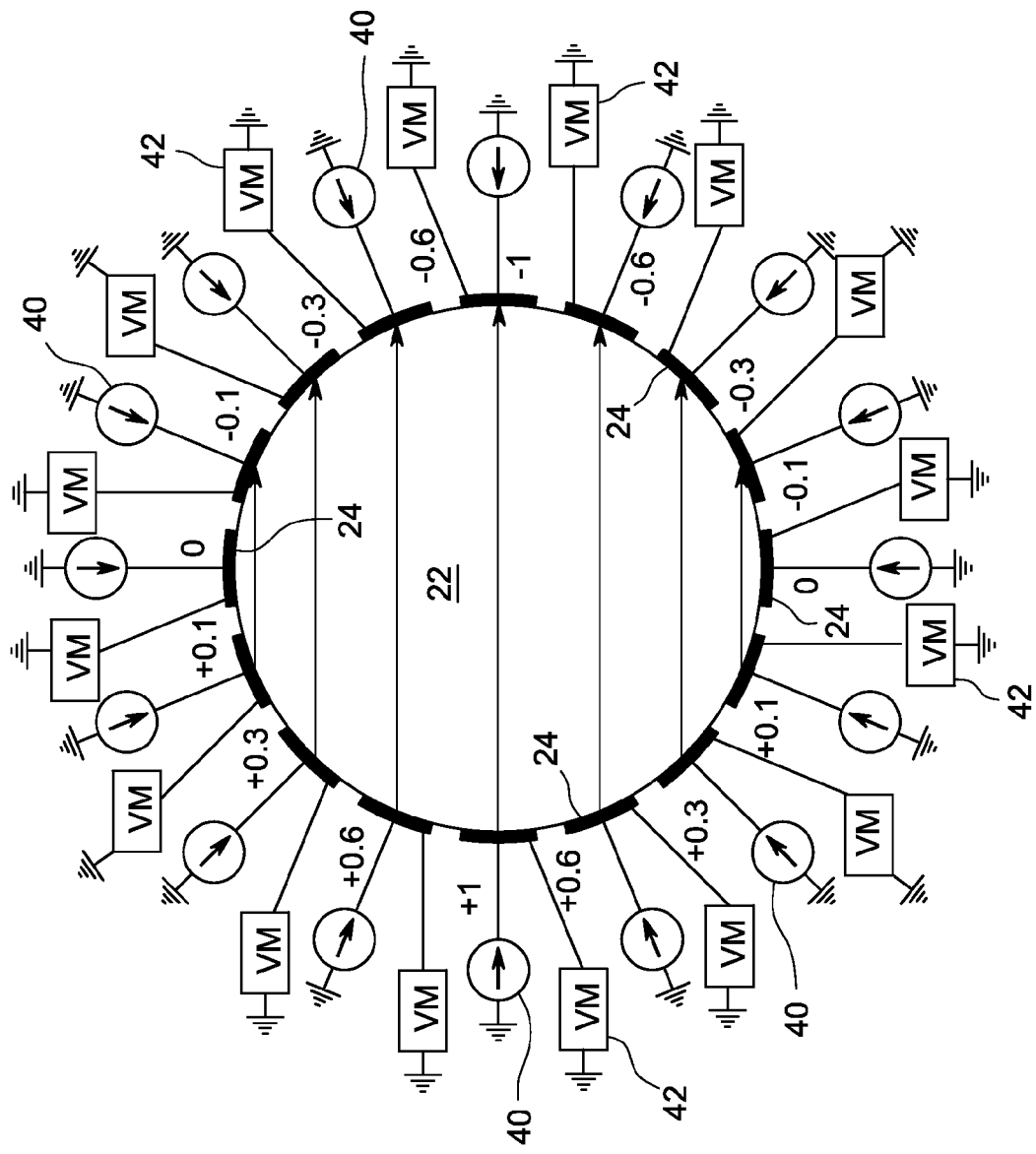
FIG. 2 is a simplified diagram illustrating one transducer configuration in accordance with various embodiments.

It should be noted that any suitable EIS method for generating distribution results for the internal structure of the object 22 may be used, such as with the processor 30 defining a geometry of the object 22, and discrediting the geometry into a structure having a plurality of nodes and elements. Thus, as illustrated in FIG. 2, the excitation driver 26 in one embodiment applies an excitation on the geometry by providing an applied current 40 on each of the transducers 24 (illustrated as electrodes), wherein the applied current 40 on each transducer 24 is derived from the same reference current source, such as the reference excitation source 36. It should be noted that current and/or voltage sources may be provided, and may be more or less than the number illustrated. For example, each transducer 24, a set of the transducers 24 or all of the transducers 24 may share a current source or voltage source. The response detector 28 is illustrated as having a plurality of voltage measuring devices, such as voltmeters 42, for measuring a voltage at the transducers 24. However, more or less voltmeters 42 may be provided or different measuring devices may be used. It should be noted that the excitation and measured response (illustrated by the values around the periphery and by the arrows within the object 22) are simplified for illustration and the excitation and corresponding conductivity distribution may be more complex (or less complex). Additionally, the illustrated values are again provided for simplicity and ease of understanding.

It should be noted that the excitations may be applied to all or a subset of the transducers 24. Similarly, any measurements may be performed at or using all or a subset of the transducers 24.

Figure 3:
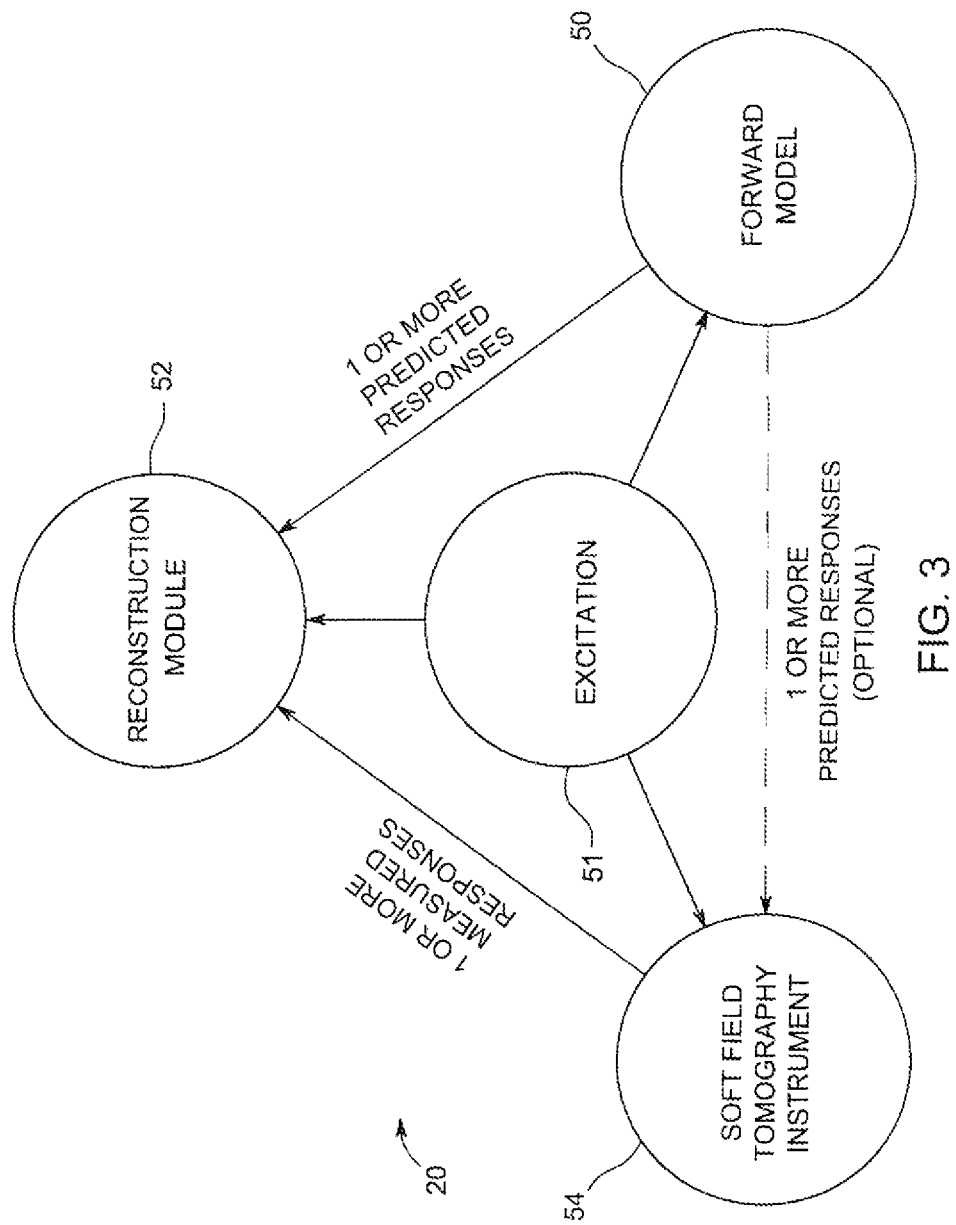
FIG. 3 is a simplified diagram illustrating data flow within a soft-field tomography system formed in accordance with various embodiments.

The processor 30 in various embodiments computes a response of the geometry to the applied excitation. The geometry is defined as including, but not limited to the shape of the boundary of the object, the location of the electrodes and the assumed conductivity distribution inside the object. For example, as illustrated in FIG. 3, the EIS system 20 uses a forward model 50 based on excitations (generally shown as EIS excitations 51) to predict responses (one or more predicated responses) that are provided to a reconstruction module 52. The excitations are applied to the object 22 (shown in FIGS. 1 and 2) via a soft-field tomography instrument 54, which include the transducers 24 and other measurement components, with measured responses (measured data, e.g., one or more measured responses) provided also to the reconstruction module 52. Using suitable EIS reconstruction methods, and as described herein, a spatial distribution of the electrical conductivity and/or permittivity of the object 22 is then derived. For example, a Newton One Step Error Reconstruct or (NOSER) or iterative solver (Gauss-Newton iterations approach) may be used by forward modeling the response and using an error term to converge to a solution. It should be noted that one or more predicted responses also optionally may be provided from the forward model 50 to the soft-field tomography instrument 54.

Figure 4:
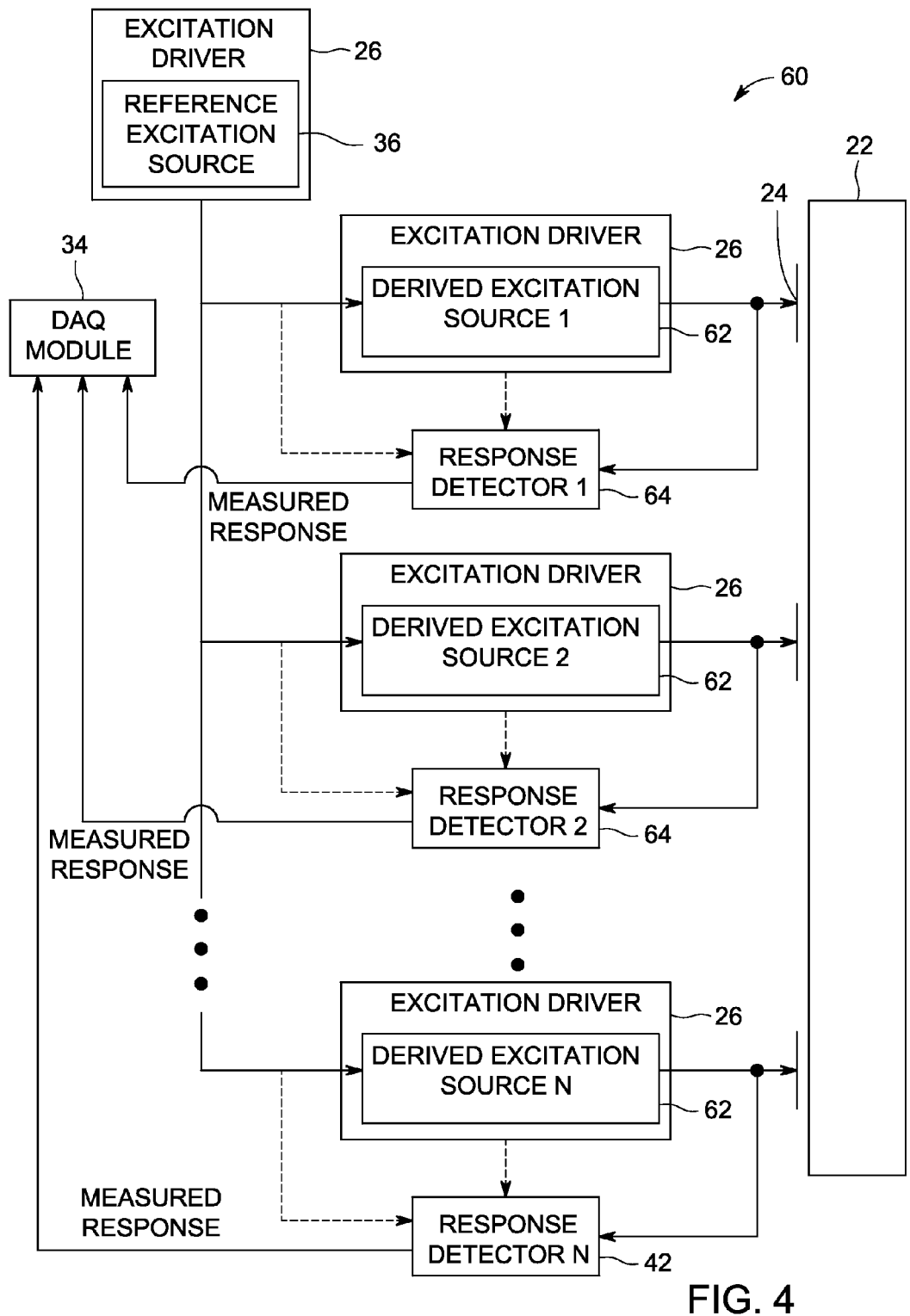
FIG. 4 is a block diagram illustrating an excitation and measurement architecture formed in accordance with various embodiments.

In accordance with various embodiments, an excitation and measurement architecture 60 shown in FIG. 4 is provided that may be integrated, for example, in a multi-channel application specific integrated circuit (ASIC), and which may be used to determine a property of an object. The multi-channel ASIC integration enables measurements, for example, of a conductivity or permittivity distribution. As can be seen, the reference excitation source 36 is used to derive, for example, derived excitation sources 62 (e.g., amplitude scaled, phase or frequency shifted excitation sources, such as current sources) for each of the plurality of transducers 24. It should be noted that current mirror architectures modified to obtain high output impedance also may be used to generate the excitation sources 62. In the illustrated embodiment, the reference excitation source 36, which may be a current excitation source, is used to derive excitation sources 62 for each channel (1 through N) corresponding to each of the plurality of transducer 24. The derived excitations from the derived excitation sources 62 are, thus, applied excitations at the transducers 24. It should be noted that the derived excitations may be derived using any suitable method that generates the same or scaled/shifted excitation for each of the plurality of transducers 24.

In this architecture 60, the measured responses may be, for example, currents and voltages that are measured and communicated to the DAQ element 34. For example, one or more response detectors 64, such as current measurement devices may measure the current received at each of the transducers 24. It should be noted that the derived excitations optionally may be provided to the response detectors 64. The current measurement device may be separate circuits or instruments connected to each of the transducers 24 or may be combined such that one current measurement device measures the current at more than one transducer 24. The current measurement device is any device or circuit capable of measuring the current, such as the instantaneous current at each of the transducers 24. As another example, a corresponding voltage measurement device may be provided to measure the output voltage at each of the transducers 24, which may be based on an impedance for each of the plurality of transducers 24. The voltage measurement device may be separate circuits or instruments connected to each of the transducers 24 or may be combined such that one voltage measurement device measures the voltage at more than one transducer 24. The voltage measurement device is any device or circuit capable of measuring voltage or impedance at each of the transducers 24.

Using the architecture 60 for the EIS system 20, a single reference excitation source is used to generate the input to the derived excitation sources 62 for each of the transducers 24 based on the excitation for the reference excitation source 36. In one embodiment, which may include calibration or tuning (or current correction) of the current applied to each of the transducers 24, the difference between the scaled/shifted reference and the individual measured responses (e.g., measured voltages) at each of the plurality of transducers 24 is measured using a number of bits that is less than the total number of bits needed for a level of precision or accuracy for the reference excitation source 36. For example, to provide the EIS system 20 with accuracy to the order of 16-bits for each of the plurality of channels, less than 16-bits of measured data from each of the plurality of transducers 24 are used. In some embodiments, with a system accuracy of 16-bits, 4-6 bit or 6-10 bit resolution measurements are used on a per channel basis.

Figure 5:
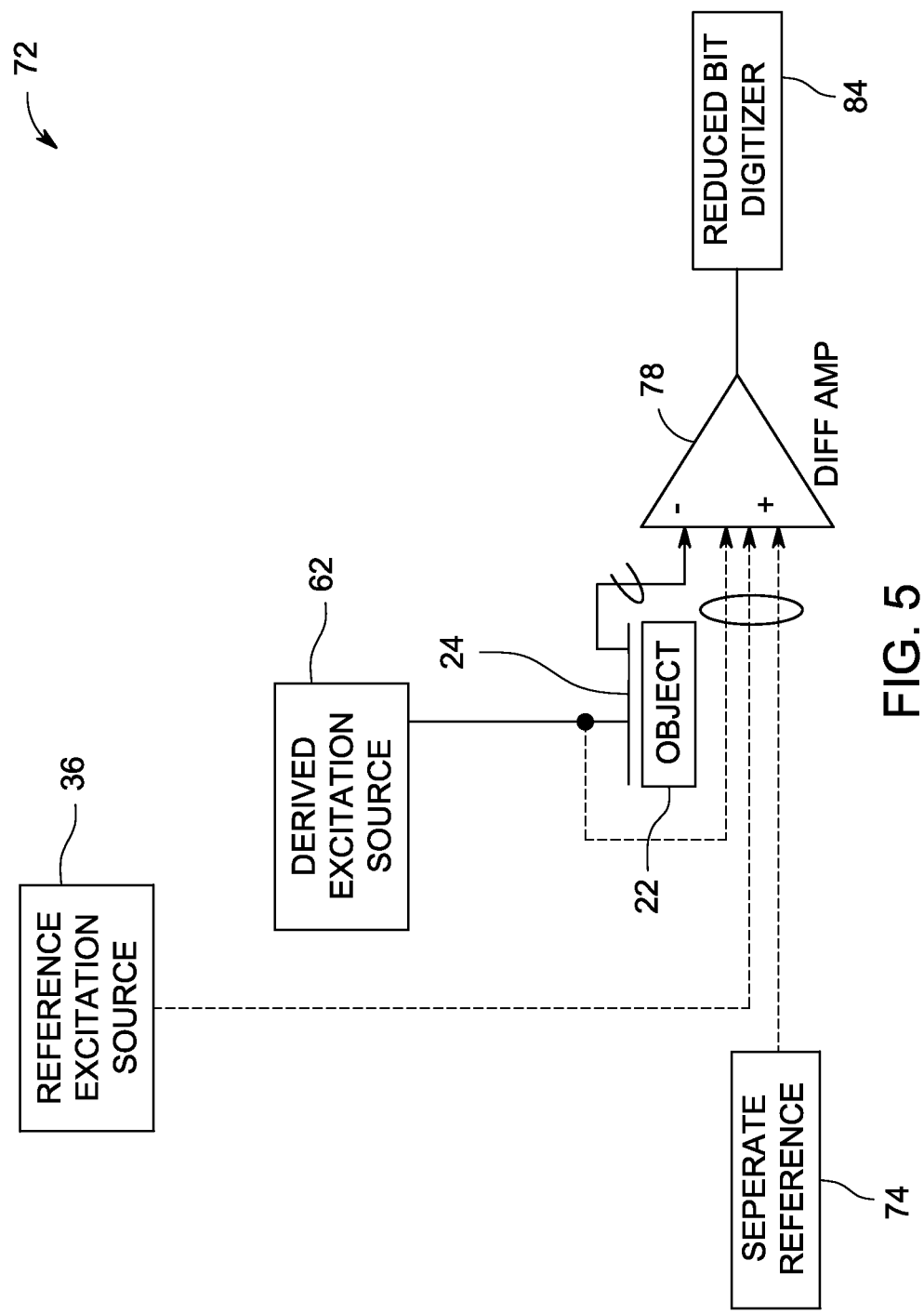
FIG. 5 is a block diagram illustrating one channel of an excitation and measurement architecture formed in accordance with various embodiments.

One embodiment of a channel 72 for the excitation and measurement architecture 60 is shown in FIG. 5. It should be noted that a plurality of channels 72 may be provided with each having a similar architecture. In this embodiment a difference operation device, which is illustrated as a differential amplifier 78 is provided. It should be noted that any suitable device for performing a difference operation may be used, and the various embodiments are not limited to the differential amplifier 78. The differential amplifier 78 receives as an input the measured response from the excitation applied to the object 22. The differential amplifier 78 also receives as an input, at least one of the derived output of the excitation source 62, the output of the reference excitation source 36 and/or the output from a separate reference source 74, for example, another reference excitation source which may provide the same or a different type of excitation than the reference excitation source. For example, the reference excitation source 36 and the separate reference 74 may each provide a reference current source, or one of the reference excitation source 36 or the separate reference 74 may provide a reference voltage source with the other providing a reference current source.

The output of the differential amplifier 78 is provided to a reduced-bit digitizer 84. For example, the reduced-bit digitizer 84 may be any device capable or receiving the analog output of the differential amplifier 78 and digitizing the analog signal to a digital signal. In various embodiments, the single reference excitation source 36 comprises an N-bit excitation source, the derived excitation source 62 comprises an X bit excitation source, and the reduced bit digitizer 84 comprises an M-bit digitizer, wherein M is less than N, M is less than X and X is less than or equal to N. Thus, in some embodiments, although the derived excitations sources and the reference excitation sources may be described as having different levels of precisions, the derived excitations sources and the reference excitation sources may have the same level of precision. It should be noted that the differential amplifier 78 and the reduced-bit digitizer 84 may be separate or integrated elements. Additionally, the number of bits for each excitation source may be different.

Figure 6:
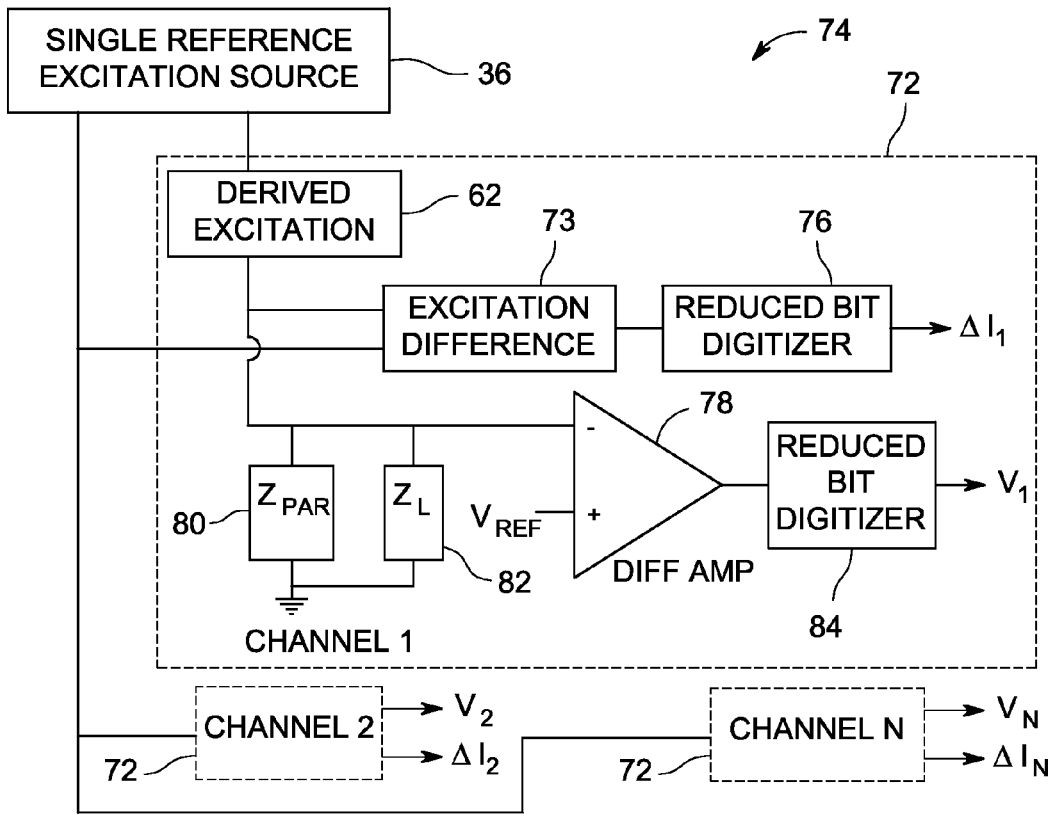
FIG. 6 is a block diagram illustrating an excitation and measurement architecture formed in accordance with other various embodiments.

As shown in FIG. 6, the single reference excitation source 36, which may be, for example, a 16-bit reference current source, is used to generate derived excitations, for example, derived currents for each of the plurality of channels 72. It should be noted that the specific components of only one of the channels 72 is shown. However, the other channels 72 may have duplicates of the same components and configuration. The excitation and measurement architecture 74 may be implemented, for example, as a current measurement device and/or a voltage measurement device. In some embodiments, the generation of the derived current source, as well as the comparison and digitization operates in a current mode (versus a voltage mode design), which allows operation at higher frequencies at the same power consumption.

As illustrated, an excitation difference measurement circuit 73, which may be a difference amplifier, such as a suitable current differencing circuit, receives at an input the excitation from the single reference excitation source 36 for the channel 72, as well as the derived excitation 62 derived from the reference excitation source 36. Thus, the excitation difference measurement circuit 73 compares the difference between the excitation from the single reference excitation source 36 and the derived excitation 62. An output of the excitation difference measurement circuit 73 is digitized to a predetermined number of bits of accuracy, for example, 4-6 bits. Accordingly, a reduced bit digitizer 76 (e.g., a reduced bit analog-to-digital converter (ADC)), is connected to the output of the excitation difference measurement circuit 73 to generate a digital excitation difference output ($\Delta I_1$) having an accuracy or resolution based on a predetermined number of bits, which may be output from the current difference measurement circuit 73. Thus, because the individual applied excitations for each of the channels 72 vary from the applied excitation derived by the reference excitation source 36 by less than the total number of bits, for example, a few bits, such as 4-6, 6-10, etc., the resolution of each channel 72 is less than the overall system resolution.

It should be noted that the reduced bit digitizer 76 may have a fixed resolution (i.e., number of bits) or an adjustable resolution, wherein the number of bits may be modified as desired or needed. Thus, the measurement from the excitation difference measurement circuit 73 may be digitized to a required or desired reduced number of bits.

In the architecture 74, the voltage output ($V_1$) is derived by the differential amplifier 78 having as inputs a response from the derived excitation 62 and a reference voltage signal ($V_{ref}$), which is a voltage representation of the predicted response and may be generated by the separate reference 74 (shown in FIG. 5), and provides a differential output. It should be noted that the applied excitation at the differential amplifier is applied to a parasitic impedance component ($Z_{PAR}$) 80 and a load impedance ($Z_L$) 82 from the object 22. The output of the differential amplifier 78 is connected to the reduced bit digitizer 84, for example, a 4-6 bit ADC, thus, having a lower accuracy (i.e., number of bits) than the reference excitation source 36.

Figure 7:
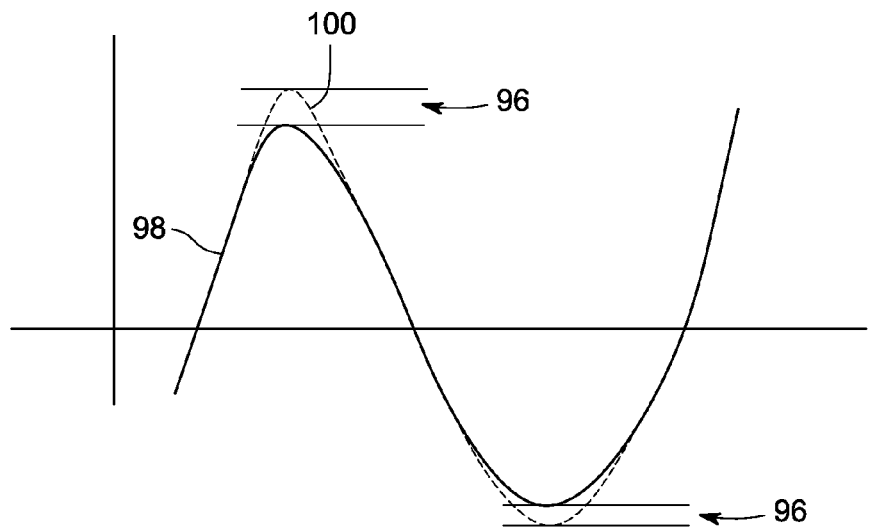
FIG. 7 is a graph illustrating exemplary waveforms used to perform difference measurements with the architecture of FIG. 6 in accordance with one embodiment.

Thus, a response may be digitized at a bit level less than the number of bits of the reference excitation source 36 because the amplitude and phase shifts determinations are only needed in small regions 96 of the waveforms 98 and 100 as shown in FIG. 7.

Figure 8:
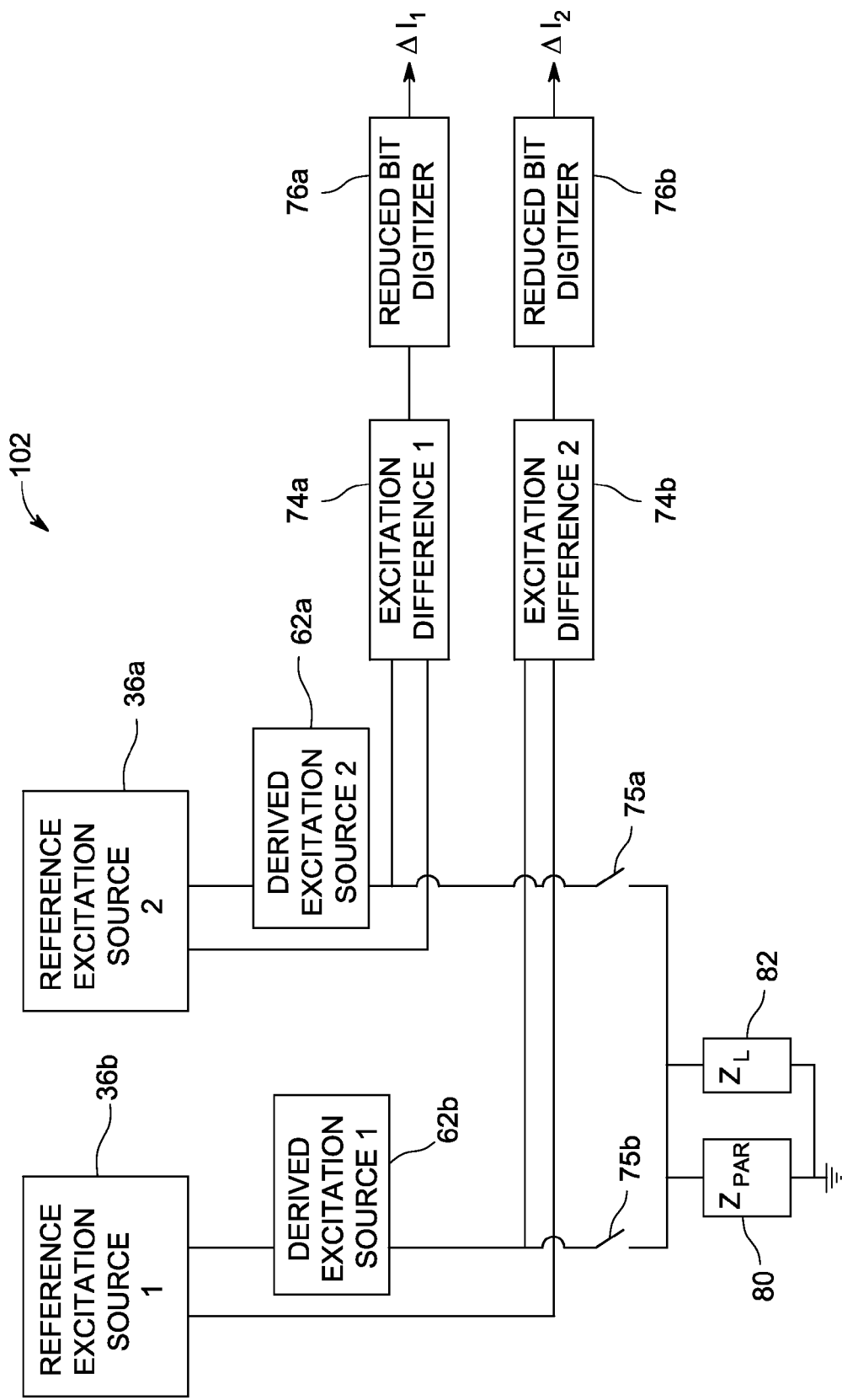
FIG. 8 is a block diagram illustrating an excitation and measurement architecture formed in accordance with other various embodiments.

Variations and modifications are contemplated. In some embodiments, an excitation and measurement architecture 102 as shown in FIG. 8 may be provided. In this embodiment, two reference excitation sources 36a and 36b are used to derive two derived excitation sources 62a and 62b (e.g., two derived currents), which may be selectively connected to the channels 72 using switches 75a and 75b connected to the two reference excitation sources 36a and 36b. Thus, this embodiment may include two calibrated current sources instead of one as provided in other embodiments. The reference excitation sources 36a and 36b may be calibrated to different loads and measure the difference between the load and the master currents for both. Accordingly, in an EIS application, two measurements are provided that are both used to solve for the real and reactive parts of the impedance without the use of any voltage measurement. It should be noted that a current mirror design optionally may be provided, which may be any suitable transistor mirror configuration, and wherein the output current may be maintained constant regardless of loading.

Thus, in accordance with various embodiments, a soft-field tomography system, for example, an impedance measurement system allows for the use of a single excitation source (used to generate derived excitation sources) and reduced bit resolution measurements to control the applied excitations, such as to calibrate or tune the applied current while still providing a required bit order accuracy (e.g., 16-bits). For example, using the relationship V=IZ, wherein V is voltage, I is current and Z is impedance, the various embodiments provide current and/or voltage matrices based on the measurements to allow for the calibrating or tuning the current source (or correcting for error), which then allows for acquiring clinically relevant impedance data. Because in various embodiments the common mode signal is removed, fewer bits are used to measure the difference.

Figure 9:
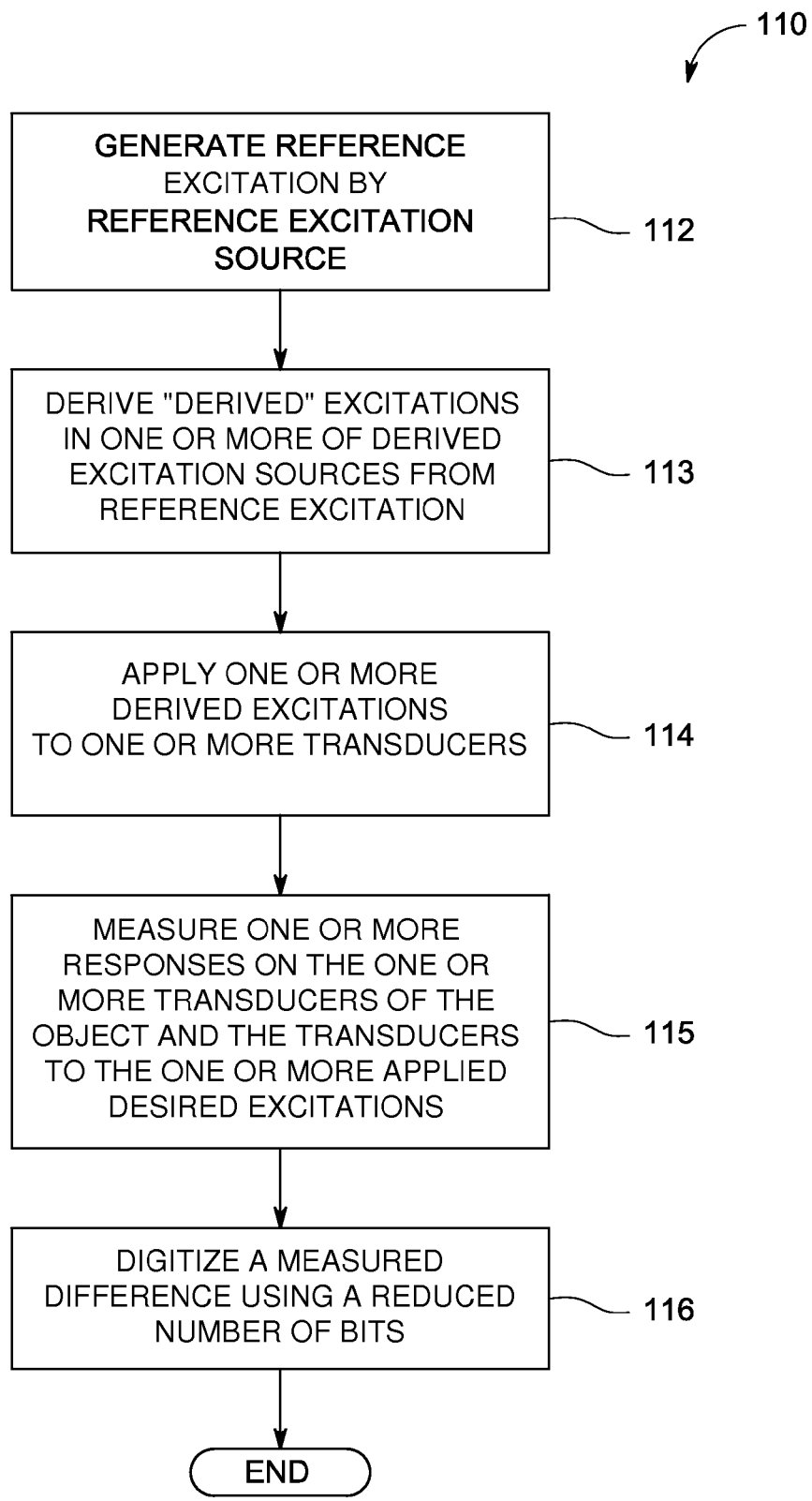
FIG. 9 is a flowchart of a method for providing soft-field tomography data acquisition in accordance with various embodiments.

A method 110 for soft-field tomography (e.g., EIS) data acquisition is shown in FIG. 9. The method 110 includes generating at 112 a reference excitation using a single reference excitation source, for example, a single reference current source (or voltage source). This may include using a single reference excitation source or two reference excitation sources. Thereafter at 113, derived excitations are derived in one or more derived excitation sources from the reference excitation and for each of the channels. For example, in an EIS system, amplitude scaled or phase or frequency shifted currents may be derived.

Thereafter, the one or more derived excitations are applied to one or more transducers at 114. Then, at 115, one or more responses are measured (i) on the one or more transducers of the object and (ii) on the transducers to the one or more applied derived excitations. For example, in some embodiments both the current and voltage difference based on a reference current source and a difference between the reference current/voltage and the derived current/voltage applied at each of the transducer, which includes using a reduced number of digitized bits, is determined. In other embodiments, a reference current/voltage source also may be used to preload the difference, such that a reduced number of bits are used to measure both the current and voltage differences. In still other embodiments, two reference current sources may be used and only the difference in current between the applied current at the transducer and the reference source is measured (twice for each channel) with no voltage measurements. It should be noted that the source difference may be used as an error term or error current to adjust the applied current at each of the channels. It should also be noted that a separate controller may be provided, for example, to control the generation of the reference excitation source or separate reference.

Thereafter, the measured difference is digitized using a reduced number of bits as described in more detail herein. Additionally, one or more material properties based on at least one applied excitation or applied excitation difference and at least one measured response or response difference may be determined, wherein the determined material properties are based on one or more of $\alpha$-mode dispersions, $\beta$-mode dispersions, $\gamma$-mode dispersions and $\delta$-mode dispersions.

Additionally, although the various embodiments are described in connection with electrical excitation, other sources of excitation may be provided. For example, optical, thermal or ultrasound excitations, among others, may be used in combination with the various embodiments.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A soft-field tomography measurement system comprising:
    a plurality of transducers configured for positioning proximate a surface of an object, wherein the plurality of transducers correspond to a plurality of channels;
    an excitation driver coupled to the plurality of channels and configured to generate excitation signals for the plurality of transducers;
    a single reference excitation source from which excitations are generated;
    one or more derived excitation sources, wherein one or more of the derived excitation sources derive excitations from the single reference excitation source and the derived excitations are applied to each of the plurality of channels;
    a response detector configured to measure a response at each of the plurality of transducers; and
    a reduced bit digitizer in each of the plurality of channels configured to digitize a measured response difference between the measured response at one or more of the transducers and at least one of an excitation of the single reference excitation source or an excitation derived from the single reference excitation source or a separate reference.

2. The soft-field tomography system of claim 1, wherein the single reference excitation source comprises an N-bit excitation source, the derived excitation source comprises an X bit excitation source and the reduced bit digitizer comprises an M-bit digitizer, wherein M is less than N, and wherein M is less than X.

3. The soft-field tomography system of claim 2, wherein N and X are each at least 12 and M is not greater than 10.

4. The soft-field tomography system of claim 1, further comprising a second reduced bit digitizer configured to digitize a measured excitation difference between a derived excitation of the single reference excitation source imposed on the transducer and a reference excitation.

5. The soft-field tomography system of claim 1, wherein the measured response at one or more of the transducers and at least one of an excitation of the single reference excitation source or an excitation derived from the single reference excitation source or a separate reference are inputs to a differential amplifier, the differential amplifier connected to the reduced bit digitizer, and wherein the reduced bit digitizer digitizes one or more measured response differences.

6. The soft-field tomography system of claim 1 wherein the single reference excitation source comprises an N-bit excitation source, the one or more derived excitation sources comprise one or more X bit excitation sources and the reduced bit digitizer that measures the response difference comprises an M-bit digitizer, wherein M is less than N, and wherein M is less than X.

7. The soft-field tomography system of claim 6, further comprising a plurality of X bit excitation sources, wherein a value of X is different for at least two of the X bit excitation sources, and M is less than X for all of the plurality of X bit excitation sources.

8. The soft-field tomography system of claim 6, wherein N and X are each at least 12 and M is not greater than 10.

9. The soft-field tomography system of claim 1, further comprising a second reference excitation source, wherein excitations are separately derived from each of the reference excitation sources for each of the plurality of channels.

10. The soft-field tomography system of claim 9, further comprising two digitizers in each of the plurality of channels configured to digitize one or more measured excitation differences between a reference excitation of at least one of each of the two reference excitation sources and the corresponding derived excitation applied at the transducer.

11. The soft-field tomography system of claim 10, further comprising at least one switch to selectively switch between the derived excitations.

12. The soft-field tomography system of claim 1, wherein the plurality of transducers is configured to acquire measured response data of an object for electrical impedance spectroscopy used to compute electrical impedance data.

13. The soft-field tomography system of claim 1, wherein the excitation driver is configured to enable one of Electrical Impedance Spectroscopy (EIS), Electrical Impedance Tomography (EIT), Diffuse Optical Tomography (DOT), Near InfraRed Spectroscopy (NIRS), thermography, elastography or microwave tomography.

14. The soft-field tomography system of claim 1, wherein the measured response is used to compute a distribution of one or more of electric conductivity, electric permittivity, magnetic permeability, optical absorbance, optical scattering, optical reflectivity, elasticity, or thermal conductivity.

15. The soft-field tomography system of claim 1, further comprising a processor configured to determine one or more material properties based on at least one applied excitation or applied excitation difference and at least one measured response or response difference, and wherein the determined material properties are based on one or more of α-mode dispersions, β-mode dispersions, γ-mode dispersions and δ-mode dispersions.

16. A multi-channel application specific integrated circuit (ASIC) comprising:
    a single reference excitation source configured to generate at least one excitation for driving each of a plurality of channels of a soft-field tomography system;
    one or more derived excitation sources, configured to generate excitations derived from the single reference excitation source;
    a response detector configured to measure a response at each of a plurality of transducers in each of the plurality of channels; and a reduced bit digitizer having fewer bits than the number of bits of the single reference excitation source and configured to digitize an output of the response detector.

17. The multi-channel ASIC of claim 16, having no positive feedback circuits.

18. The multi-channel impedance measurement ASIC of claim 16, further comprising a processor configured to determine a property of an object based on at least one applied excitation or applied excitation difference and at least one measured response or response difference.

19. The multi-channel ASIC of claim 18, wherein the determined property is based on one of measured $\alpha$-mode dispersions, $\beta$-mode dispersions, $\gamma$-mode dispersions and $\delta$-mode dispersions.

20. The multi-channel ASIC of claim 16, further comprising a processor configured to determine an electrical impedance based on at least one applied excitation or applied excitation difference and at least one measured response or measured response difference.

21. A method for providing excitation and data acquisition for a soft-field tomography system, the method comprising:

deriving one or more excitations from at least one reference excitation source which are applied to a plurality of channels of the soft-field tomography system;

measuring at least one difference between the excitation applied at one or more transducers corresponding to the plurality of channels and a reference excitation; and digitizing the measured difference using a reduced number of data bits.

22. The method of claim 21, further comprising calibrating the excitation to the plurality of transducers based on the measured difference.

23. The method of claim 21, wherein deriving the derived excitations comprises one or more of amplitude scaling, frequency shifting or phase shifting.

* * * * *